US010251546B2

(12) United States Patent
Foss

(10) Patent No.: US 10,251,546 B2
(45) Date of Patent: Apr. 9, 2019

(54) APPARATUS AND METHODS FOR THE TREATMENT OF OCULAR DISORDERS

(71) Applicant: NOTTINGHAM UNIVERSITY HOSPITALS NHS TRUST, Nottingham (GB)

(72) Inventor: Alexander James Easterbrook Foss, Nottingham (GB)

(73) Assignee: Nottingham University Hospitals NHS Trust, Nottingham (GB)

( * ) Notice: Subject to any disclaimer, the term of this patent is extended or adjusted under 35 U.S.C. 154(b) by 238 days.

(21) Appl. No.: 15/127,668

(22) PCT Filed: Mar. 18, 2015

(86) PCT No.: PCT/GB2015/050790
§ 371 (c)(1),
(2) Date: Sep. 20, 2016

(87) PCT Pub. No.: WO2015/145111
PCT Pub. Date: Oct. 1, 2015

(65) Prior Publication Data
US 2018/0168444 A1 Jun. 21, 2018

(30) Foreign Application Priority Data
Mar. 24, 2014 (GB) .................. 1405232.8

(51) Int. Cl.
A61B 3/08 (2006.01)
A61B 3/032 (2006.01)
A61B 3/113 (2006.01)
A61B 3/024 (2006.01)
A61B 3/11 (2006.01)

(52) U.S. Cl.
CPC ............... *A61B 3/08* (2013.01); *A61B 3/024* (2013.01); *A61B 3/032* (2013.01); *A61B 3/113* (2013.01); *A61B 3/11* (2013.01)

(58) Field of Classification Search
CPC .......... A61B 3/08; A61B 3/032; A61B 3/113; A61B 3/02; A61H 5/00
USPC ........................................ 351/201
See application file for complete search history.

(56) References Cited

U.S. PATENT DOCUMENTS

| 2,124,229 A | 7/1938 | Errol et al. |
| 2,495,263 A | 1/1950 | Korb et al. |
| 3,883,234 A | 5/1975 | Lynn et al. |

(Continued)

FOREIGN PATENT DOCUMENTS

| DE | 10013682 A1 | 10/2001 |
| EP | 2 636 360 A1 | 9/2013 |

(Continued)

OTHER PUBLICATIONS

Slack et al., "The Measurement and Treatment of Suppression in Amblyopia," J. Vis. Exp. 70:e3927 (2012).

(Continued)

*Primary Examiner* — Mohammed A Hasan
(74) *Attorney, Agent, or Firm* — Pepper Hamilton LLP

(57) ABSTRACT

Apparatus for the assessment of visual function and ocular motility and the treatment of disorders thereof, comprising ocular display apparatus which presents different, but visually related, images to each eye. The invention also relates to methods of assessment of ocular disorders and to their treatment.

21 Claims, 3 Drawing Sheets

(56) References Cited

U.S. PATENT DOCUMENTS

| | | | |
|---|---|---|---|
| 4,818,091 | A | 4/1989 | Sadun et al. |
| 5,061,060 | A | 10/1991 | Aulhorn et al. |
| 2004/0057013 | A1 | 3/2004 | Cappo et al. |
| 2005/0001980 | A1* | 1/2005 | Spector .............. A61B 5/04842 351/203 |
| 2006/0087618 | A1 | 4/2006 | Smart et al. |
| 2012/0069296 | A1 | 3/2012 | Li et al. |
| 2012/0127426 | A1* | 5/2012 | Backus ................ A61H 5/005 351/203 |
| 2012/0307203 | A1* | 12/2012 | Vendel ................ A61B 3/085 351/201 |
| 2013/0162944 | A1 | 6/2013 | Fateh |
| 2013/0258463 | A1 | 10/2013 | Evans et al. |

FOREIGN PATENT DOCUMENTS

| | | | |
|---|---|---|---|
| GB | 2495697 | A | 4/2013 |
| RU | 2282423 | C2 | 8/2006 |
| WO | 2003/092482 | A1 | 11/2003 |
| WO | 2008/070683 | A1 | 6/2008 |
| WO | 2014041545 | A1 | 3/2014 |

OTHER PUBLICATIONS

Cleary et al., "Assessment of a Computer-Based Treatment for Older Amblyopes: The Glasgow Pilot Study," Eye 23:124-31 (2009).

Eastgate et al., "Modified Virtual Reality Technology for Treatment of Amblyopia," Eye 20:370-74 (2006).

Herbison et al., "Interactive Binocular Treatment (I-BiT) for Amblyopia: Results of a Pilot Study of 3D Shutter Glasses System," Eye 27:1077-83 (2013).

Hess et al., "A New Binocular Approach to the Treatment of Amblyopia in Adults Well Beyond the Critical Period of Visual Development," Restor. Neurol. Neurosci. 28:793-802 (2010).

Hess et al., "An iPod Treatment for Amblyopia: An Updated Binocular Approach," Optometry 15:87-94 (2012).

Knox et al., "An Exploratory Study: Prolonged Periods of Binocular Stimulation Can Provide an Effective Treatment for Childhood Amblyopia," Invest. Ophthalmol. Vis. Sci. 53:817-24 (2012).

Mansouri et al., "Measurement of Suprathreshold Binocular Interactions in Amblyopia," Vision Research 48:2775-84 (2008).

To et al., "A Game Platform for Treatment of Amblyopia," IEEE Transactions on Neural Systems and Rehabilitation Engineering 19:280-9 (2011).

Waddingham et al., "Preliminary Results From the Use of the Novel Interactive Binocular Treatment (I-BiT) System, in the Treatment of Strabismic and Anisometropic Amblyopia," Eye 20:375-8 (2006).

International Preliminary Report on Patentability corresponding to PCT/GB2015/050790, dated Sep. 27, 2016.

International Search Report and Opinion corresponding to PCT/GB2015/050790, dated Oct. 13, 2015.

Great Britain Search Report corresponding to GB1405232.8, dated Sep. 29, 2014.

* cited by examiner

= Point of gaze of normal eye as determined by eye-tracker

= Point of gaze of amblyopic eye

= Point of gaze of normal eye as determined by eye-tracker

= Point of gaze of amblyopic eye

APPARATUS AND METHODS FOR THE TREATMENT OF OCULAR DISORDERS

This application is a national stage application under 35 U.S.C. § 371 of PCT Application No. PCT/GB2015/050790, filed Mar. 18, 2015, which claims the priority benefit of Great Britain Application No. 1405232.8, filed Mar. 24, 2014.

BACKGROUND OF THE INVENTION

This invention relates to apparatus which may be used to assess visual function and ocular motility, and to treat disorders thereof. The invention also relates to methods of treatment of such disorders that involve the use of that apparatus.

In particular, the invention relates to ocular display apparatus which presents different, but visually related, images to each eye. The invention also relates to methods of assessment of ocular disorders and to their treatment.

There are a number of common eye conditions in which a person's eyes fail to work correctly in combination with each other. These conditions can result in blurred or double vision, or the absence of true stereovision.

Such conditions are often the result of physical problems, ie strabismus, commonly known as a squint, which can result in amblyopia, commonly known as "lazy eye".

This invention has particular relevance to the assessment and treatment of amblyopia. However, the invention may also be applicable to the study and treatment of many other eye conditions, and vision/coordination related brain problems (particularly for survivors of stroke), or neurological pathway developmental problems.

Amblyopia is a condition of the visual system in which one eye fails to develop a normal level of visual acuity during the developmental period for vision. Amblyopia can occur in subjects who are strabismic (have a squint) or have anisometropia (such that both eyes have different refractive errors, leaving one eye defocused), or a combination of both (mixed amblyopia). Amblyopia can also arise from stimulus deprivation (for example, as a result of having a cataract). The poor vision resulting from amblyopia does not always resolve even when the underlying condition has been treated.

Amblyopia is a common condition of childhood, affecting perhaps as many as 2-3 percent of the population, and can carry over into adult life if left untreated. Whilst most people can manage with a lazy eye, they may well have reduced or no binocular function and this may compromise their ability to perform certain complex tasks, such as flying an aeroplane or driving a train. Furthermore, persons with one amblyopic eye who suffer injury to their "normal" eye may be effectively blind.

A person's visual field can be divided into peripheral and central vision. In amblyopia, the peripheral vision is normal but there is a defect in the central vision with reduced sensitivity to detection of stimuli with high spatial frequency, which is reflected in reduced visual acuity, and the presence of a central area of reduced visual sensitivity (scotoma).

Whilst many treatments for amblyopia have been attempted, the most common remains the use of a patch, which has been advocated for decades. Indeed, use of a patch for this purpose was documented as early as the eighteenth century. In such treatments, the non-amblyopic eye is covered with a patch for prescribed periods of time daily (eg several hours each day) over a protracted period, perhaps for several months or even years. The patching of the non-amblyopic eye forces the wearer to use the amblyopic eye, and hence that eye is stimulated, leading to an improvement in function. A major drawback with the use of the patch, however, is poor subject compliance where the subject does not wear the patch for the prescribed time periods.

Most subjects treated in this way are children. Many children do not wear the patch as directed, for instance because their vision is much poorer when using only the lazy eye, or because they are teased when wearing the patch and so remove it. Non-compliance is a major cause of failure of the patching technique in treating children with amblyopia.

An alternative treatment is penalisation, in which the vision in the normal eye is blurred by the administration of atropine drops. This treatment was introduced in the $19^{th}$ century and is less commonly used than patching, but the reported results are similar.

It is thought that children with amblyopia are best treated before the age of eight years. Patients with amblyopia who are over the age of 12 years do not respond to patching or penalisation.

Dichoptic stimulation, the presentation of different images to each eye, has been shown to be effective in the treatment of amblyopia. See WO03/092482, which describes an ocular display apparatus having image presentation means adapted to display a first image to one eye only of a subject, and a second, different image to the other eye only. The first and second images are presented to the subject so that they perceive a composite image, at least one of the first and second images including a moving object. The apparatus is useful in the treatment of amblyopia and other ocular disorders. However, a major limitation of this apparatus is an inability to compensate for the presence of strabismus.

BRIEF SUMMARY OF THE INVENTION

There have now been developed improved apparatus and methods for treating ocular disorders, which overcome or substantially mitigate the above-mentioned and/or other shortcomings and disadvantages of the prior art.

The improved apparatus retains the ability to present different images simultaneously to both eyes (dichoptic stimulation). The apparatus will allow selective degradation of the image presented to one eye and this degradation can take the form a blurred patch or selective removal of features of interest or the addition of masking to obscure aspects of the scene presented. The apparatus has the capacity to alter the degree of degradation in real time. The apparatus also includes eye-tracking capability and has the ability to monitor, and record, eye positions in real time and to be able to alter the image presentations in response to eye-movements.

The incorporation of eye-tracking technology into the apparatus allows for three major improvements in the management of patients with strabismus.

The first improvement is the ability to measure the size and degree of the scotoma in the amblyopic eye. The test requires the ability to present images separately to each eye (dichoptic stimulation) combined with the ability to track eye movement. This allows the image to the normal eye to be degraded by a slowly increasing amount until the patient shifts the fixing eye from the normal to the amblyopic eye. This movement of the eyes can be detected by the eye tracker. The level of image degradation at the time point when the eye-movement is detected represents the end-point of the test and this level of degradation is recorded as the test result.

This test process may then be reversed. The quality of the image to the normal eye is then slowly restored until the point when the normal eye again becomes the fixing eye. The ocular movement associated with this movement is again detected and the degree of degradation at this time point represents the end-point of the test and this degree of degradation is recorded.

The size of the scotoma can be determined by increasing the area of image degradation until there is an eye movement associated with a shift in fixation from the normal eye to the amblyopic eye. The degree or depth of the scotoma can be determined, for a fixed size, by increasing the amount of image degradation in the test area until there is an eye movement associated with a shift in fixation from the normal eye to the amblyopic eye. The size and the depth of the scotoma are variables that can be independently varied.

Existing tests are all based on the amblyopic eye taking up fixation using neutral density filters placed in front of the fixing eye to progressively dim a fixation target. The ability to measure the scotoma size and depth on the basis of eye movements is novel as is the ability to measure loss of fixation by the amblyopic eye. These are useful new measures for planning and monitoring response to treatment.

The eye-tracking allows presentation of the area of image degradation to be in a fixed relationship to the point of fixation. There is a difference in central and peripheral vision and this allows degradation of the image to selectively affect the central vision. In amblyopia, the defect predominantly affects the central vision. However in other conditions, the defect can take a different pattern. For example, in stroke patients in can affect the right or the left half of the visual field (termed hemianopia).

A further advantage of this apparatus is that the subject is visually immersed in the displayed images.

DETAILED DESCRIPTION OF THE INVENTION

According to a first aspect of the present invention, there is provided apparatus for use in the treatment of strabismic amblyopia in a subject having a non-amblyopic eye that performs better and an amblyopic eye that performs worse, the amblyopic eye having a central scotoma, the apparatus comprising image presentation means adapted to display a first image to the non-amblyopic eye and a second image to the amblyopic eye, the first and second images being presented to the subject so as to be perceived as coincidental, wherein the first image and the second image include a common background, the apparatus further comprising eye-tracking means adapted to monitor the direction of gaze of the non-amblyopic eye and the amblyopic eye on the first and second images respectively, the apparatus further comprising means for creating a region of degradation at the point of fixation of the first image, and for increasing the area of said region of degradation, wherein, in use of the apparatus, the non-amblyopic eye is fixed on the point of fixation prior to creation of the region of degradation and until the area of the region of degradation reaches a certain magnitude, whereupon the amblyopic eye takes up fixation, fixation of the amblyopic eye being indicated by a change in the direction of gaze of the amblyopic eye detected by the eye-tracking means, and the area of said region of degradation at which said take-up of fixation by the amblyopic eye occurs providing an indication of the size of the central scotoma of the amblyopic eye.

By "visually immersed" is meant that the subject sees substantially only the displayed images. The subject has no significant peripheral vision outside the displayed images, and so is not readily visually distracted by incidental movement in their peripheral vision. This is particularly important if children are the subjects, as they are easily distracted. When the subject is visually immersed, it is possible to study and treat defects of peripheral vision, as can occur, for example, in survivors of stroke with hemianopia.

The apparatus may comprise image presentation means configured as one or more screens. Preferably, the image presentation means are configured as first and second screens on which the first and second images are respectively displayed, and may include a barrier means adapted to allow each eye of a subject to see only a respective first or second screen, and to prevent each eye of the subject from seeing the other of the first or second screens. Alternatively, the images may be presented on discrete parts of a single screen, each eye being able to see only a respective one of the images.

Alternatively, the image presentation means may include a projector adapted to project the first and second images. First and second screens may be provided on which the first and second images are respectively projected.

Alternatively, or additionally, the image may be generated in some other way, for example using a CRT screen, a plasma screen or an LCD (liquid crystal display).

Most preferably, the image may be generated on a pixellated screen in which the pixels are individually electronically addressed, for example one which employs a raster array.

Most preferably, the first and second images are presented to the subject alternately, sufficiently rapidly as to be perceived to be simultaneously and continuously displayed.

Preferably, the first and second images are substantially identical, the images differing from each other only in the manner described herein, ie the first image may contain some degradation of a fixation feature and the second image may be angularly displaced relative to the first image.

The image presentation means, by which the first and second images are displayed to the non-amblyopic and amblyopic eyes respectively, may function by any of numerous technologies. Most conveniently, however, the image presentation means involves alternate frame sequencing, in which the first and second images are displayed alternately on a visual display unit, the images alternating in accordance with the refresh rate of the unit. An active shutter system is then used to present the first and second images separately to the user's eyes. The active shutter system may be incorporated into a pair of "shutter glasses", of the general type that are used to create a perception of three-dimensionality in certain films and video games. Essentially, shutter glasses comprise a pair of eyeglasses arranged, in use, in front of the subject's eyes, such that each eye can see only the image transmitted through the eyeglass in front of it. Typically, the shutter glasses incorporate a physical barrier between the eyeglasses, e.g. fitting closely to the bridge of the wearer's nose, to prevent each eye seeing the image that is intended for presentation to the other eye.

The shutter glasses function by repeatedly presenting the first image to the non-amblyopic eye while blocking the second image, and then presenting the second image to the amblyopic eye while blocking the first image. This process is repeated sufficiently rapidly that the images are perceived by the wearer of the shutter glasses as continuous.

In order to achieve the alternate blocking of the eyeglasses in front of the non-amblyopic and amblyopic eyes, each eyeglass will typically incorporate a layer of liquid crystalline material that has the property of becoming opaque when a voltage is applied to it, being otherwise transparent (or vice versa). The timing of the switching of each eyeglass between the opaque and transparent states is synchronised with the refresh rate of the visual display unit, and the first and second images are displayed alternately on the visual display unit. Thus, when the first image is displayed, the eyeglass in front of the amblyopic eye is in its opaque state and that in front of the non-amblyopic eye is transparent, so that the first image is seen only by the non-amblyopic eye. Then, the second image is displayed, with the eyeglass in front of the non-amblyopic eye in the opaque condition and that in front of the amblyopic eye transparent, so that the second image is seen only by the amblyopic eye.

The rate of alternation between the opaque and transparent states for each eyeglass should be sufficient to avoid any perception of flicker in the respective images. Shutter glass technology is available with a switching frequency of 120 Hz, ie 60 images per eye per second, and this is generally considered to be flicker-free. Thus, switching rates of that frequency, or higher, are considered to be suitable for use in the present invention.

The patient would still wear their own refractive correction and the shutter glasses would be worn over their normal spectacle correction.

Those with large angle strabismus (in excess of 40 prism dioptres) pose a technical problem for eye-tracking. This can be overcome by the placing of a prism in front of one or both lenses of the shutter glasses. The use of prisms reduces the apparent angle of the strabismus by the value of the prism, and thereby brings the angle of deviation down to within the range that would allow accurate tracking of both eyes.

However, the principles outlined in this application can be adapted to any method capable of performing dichoptic stimulation and is not just restricted to the shutter glasses technology. In particular, the same image dichoptic image presentation can be achieved with head mounted displays which are also compatible with eye-tracking technology.

The fixation feature is typically a part of the first and second images that has relatively high spatial frequency. For instance, the fixation feature may include a regular pattern of visual elements such as lines or some other geometric pattern. In other instances, the fixation feature may be a feature of the image that attracts the eye due to its significance in the context of the images. For example, the images may be moving images, such as an animation or video game and the fixation feature may be character in that animation or game.

The degradation that is created in the fixation feature seen by the non-amblyopic eye is most conveniently a blurring of that feature. The blurring will generally occur in a circular or generally circular area of the fixation feature, the diameter of the blurred area gradually being increased until the amblyopic eye takes up fixation.

Blurring may be brought about using a low-pass filter constrained within a Gaussian envelope. At its simplest, the blurring may be brought about by simply averaging the luminance of all the pixels within the region of degradation.

It is also possible to blur specific features. Face recognition is now a mature technology and it is possible to detect and selective degrade faces in the presented image, or any other feature(s) of interest.

The apparatus of the invention incorporates eye-tracking means for monitoring the direction of gaze of the non-amblyopic eye and the amblyopic eye on the first and second images. Such means generally comprises means for tracking the movement of the eyes, ie means for monitoring either the point of gaze (where the subject is looking) or the motion of an eye relative to the head.

The means for tracking the movement of the eyes may include video cameras that are focused on the eyes and record their movement as the subject views the first and second images. It may alternatively be possible for a single video camera to monitor the movement of both eyes, but in preferred embodiments of the invention, the movement of the two eyes are monitored independently. In many such systems, the centre of the pupil and infra-red, non-collimated light are used to create corneal reflections. The vector between the pupil centre and the corneal reflections can be used to compute the point of regard on the observed image or the gaze direction.

The eye-tracking technique used may be of the type generally referred to as "bright-pupil" or "dark-pupil". These techniques differ in the location of the illumination source with respect to the optics. If the illumination is coaxial with the optical path, then the eye acts as a retroreflector as the light reflects off the retina. This is "bright pupil" tracking. On the other hand, if the illumination source is offset from the optical path, then the pupil appears dark because the retroreflection from the retina is directed away from the camera. This is "dark-pupil" tracking.

The eye-tracking cameras may be incorporated into shutter glasses that are worn by the subject. Alternatively, the cameras may be fixed to the screen on which the images are displayed and tracking performed through the shutter glasses.

Where the first and second images are static images, the position of the fixation feature will be constant. Nonetheless, the direction of gaze of the subject's non-amblyopic eye may change as the subject explores the image. The eye-tracking cameras enable the direction of gaze to be monitored, and hence enable the region of degradation to be moved accordingly within the image, so as to ensure that the region of degradation is continually aligned with the direction of gaze of the normal eye.

Displacement of the region of degradation in this manner will also normally be required where the images are moving images, eg where the images are part of a computer game or other animation. The fixation feature in such a situation may be a character that moves around within the image. Indeed, the position of the character (ie the fixation feature) within the image may be controlled by the subject, for instance where the image is part of an interactive computer game.

As described above, the apparatus according to the first aspect of the invention may be used to estimate the size and degree of the central scotoma in a patient suffering from strabismic amblyopia. This information can then be used to set the size of the area and the degree of image degradation for the treatment.

Thus, in a related, second, aspect of the invention, there is provided a method for determining the size of the central scotoma of the amblyopic eye of a subject having a non-amblyopic eye that performs better and an amblyopic eye that performs worse, the method comprising presenting a first image to the non-amblyopic eye and a second image to the amblyopic eye, the first and second images being presented to the subject so as to be perceived as coincidental, and the first image and the second image including a common background, creating a region of degradation within a fixation feature of the first image, and increasing the area of said region of degradation until the amblyopic eye takes up fixation, wherein the non-amblyopic eye is fixed on the fixation feature prior to creation of the region of degradation and until the area of the region of degradation reaches a certain magnitude, whereupon the amblyopic eye takes up fixation, the area of said region of degradation when the amblyopic eye takes up fixation providing an indication of the size of the central scotoma of the amblyopic eye.

As described above, the taking up of fixation by the amblyopic eye can be detected by tracking the movement of the amblyopic eye. As the patient is strabismic, the take-up of fixation will generally be accompanied by a change in the direction of gaze of the amblyopic eye, and detection of that movement provides an indication of the critical size of the region of degradation (ie the size of the region of degradation that causes the amblyopic eye to take up fixation), and hence of the size of the central scotoma.

Not only does the movement of the amblyopic eye provide an indication of the size of the central scotoma in that eye, but the magnitude of the change in the direction of gaze also provides an indication of the severity of the subject's strabismus, ie of the angle of squint. This information may be utilised in the treatment of the strabismus.

According to a third aspect of the invention, there is thus provided apparatus for use in the treatment of strabismic amblyopia in a subject having a non-amblyopic eye that performs better and an amblyopic eye that performs worse, the amblyopic eye having a central scotoma, the apparatus comprising
image presentation means adapted to display a first image to the non-amblyopic eye and a second image to the amblyopic eye, the first and second images being presented to the subject so as to be perceived as a composite image, wherein the first image and the second image include a common background, the apparatus further comprising means for creating a region of degradation within a fixation feature of the first image, and the apparatus further comprising means for angularly displacing the second image relative to the first image by an angle corresponding to the subject's angle of squint, such that harmonious retinal correspondence is achieved.

A related, fourth, aspect of the invention provides a method for the treatment of strabismic amblyopia in a subject having a non-amblyopic eye that performs better and an amblyopic eye that performs worse, the amblyopic eye having a central scotoma, the method comprising presenting a first image to the non-amblyopic eye and a second image to the amblyopic eye, the first and second images being presented to the subject so as to be perceived as a composite image, and the first image and the second image including a common background, wherein a region of degradation is created within a fixation feature of the first image, and wherein the second image is angularly displaced relative to the first image by an angle corresponding to the subject's angle of squint, such that harmonious retinal correspondence is achieved.

The apparatus and method according to the third and fourth aspects of the invention permit the development of peripheral harmonious retinal correspondence, yet stimulate the amblyopic eye as a result of the degradation of the fixation feature of the first image. In general, the region of degradation will have a sufficient area, as determined by the method of the second aspect of the invention, to cause the amblyopic eye to take up fixation. This ensures that the amblyopic eye is stimulated.

It will be appreciated that same apparatus may be used for both assessment of the size and degree of the central scotoma of the amblyopic eye and for the treatment of strabismic amblyopia. Thus, in a specific aspect of the invention, there is provided apparatus for use in the treatment of strabismic amblyopia in a subject having a non-amblyopic eye that performs better and an amblyopic eye that performs worse, the amblyopic eye having a central scotoma, the apparatus comprising image presentation means adapted to display a first image to the non-amblyopic eye and a second image to the amblyopic eye, wherein the first image and the second image include a common background, the apparatus further comprising eye-tracking means adapted to monitor the direction of gaze of the non-amblyopic eye and the amblyopic eye on the first and second images respectively, the apparatus further comprising means for creating a region of degradation within a fixation feature of the first image, and for increasing the area of said region of degradation, and the apparatus further comprising means for angularly displacing the second image relative to the first image by an angle corresponding to the subject's angle of squint, such that harmonious retinal correspondence is achieved, wherein, in a first mode of use of the apparatus, the non-amblyopic eye is fixed on the fixation feature prior to creation of the region of degradation and until the area of the region of degradation reaches a certain magnitude, whereupon the amblyopic eye takes up fixation upon the fixation feature, fixation of the amblyopic eye being indicated by a change in the direction of gaze of the amblyopic eye detected by the eye-tracking means, and the area of said region of degradation at which said take-up of fixation by the amblyopic eye occurs providing an indication of the size of the central scotoma of the amblyopic eye, and wherein, in a second mode of use of the apparatus, a region of degradation is created within the fixation feature of the first image, said region of degradation being of sufficient size to cause the amblyopic eye to take up fixation, and the second image is angularly displaced relative to the first image by an angle corresponding to the subject's angle of squint, such that harmonious retinal correspondence is achieved.

Likewise, the invention provides a method for the treatment of strabismic amblyopia in a subject having a non-amblyopic eye that performs better and an amblyopic eye that performs worse, the method comprising a) determining the size of the central scotoma of the amblyopic eye of the subject, by a1) presenting a first image to the non-amblyopic eye and a second image to the amblyopic eye, the first and second images being presented to the subject so as to be perceived as coincidental, and the first image and the second image including a common background, a2) creating a region of degradation within a fixation feature of the first image, and increasing the area of said region of degradation until the amblyopic eye takes up fixation, wherein the non-amblyopic eye is fixed on the fixation feature prior to creation of the region of degradation and until the area of the region of degradation reaches a certain magnitude, whereupon the amblyopic eye takes up fixation, the area of said region of degradation when the amblyopic eye takes up fixation providing an indication of the size of the central suppression scotoma of the amblyopic eye, a3) detecting a change in the direction of gaze of the amblyopic eye that is indicative of the amblyopic eye taking up fixation, and measuring the angular change in the direction of gaze; and b) treating the strabismic amblyopia, by b1) presenting a first image to the non-amblyopic eye and a second image to the amblyopic eye, the first and second images being presented to the subject so as to be perceived as a composite image, and the first image and the second image including a common background, b2) creating a region of degradation within a fixation feature of the first image, the size of the region of degradation being at least as great as that determined in step a) to cause the amblyopic eye to take up fixation, and b3) angularly displacing the second image relative to the first image by an angle corresponding to the angular change in the direction of gaze measured in step a3), such that harmonious retinal correspondence is achieved.

BRIEF DESCRIPTION OF THE DRAWINGS

The invention will now be described in greater detail, by way of illustration only, with reference to the accompanying drawings, in which.

DETAILED DESCRIPTION OF PREFERRED EMBODIMENTS

Figure 1:
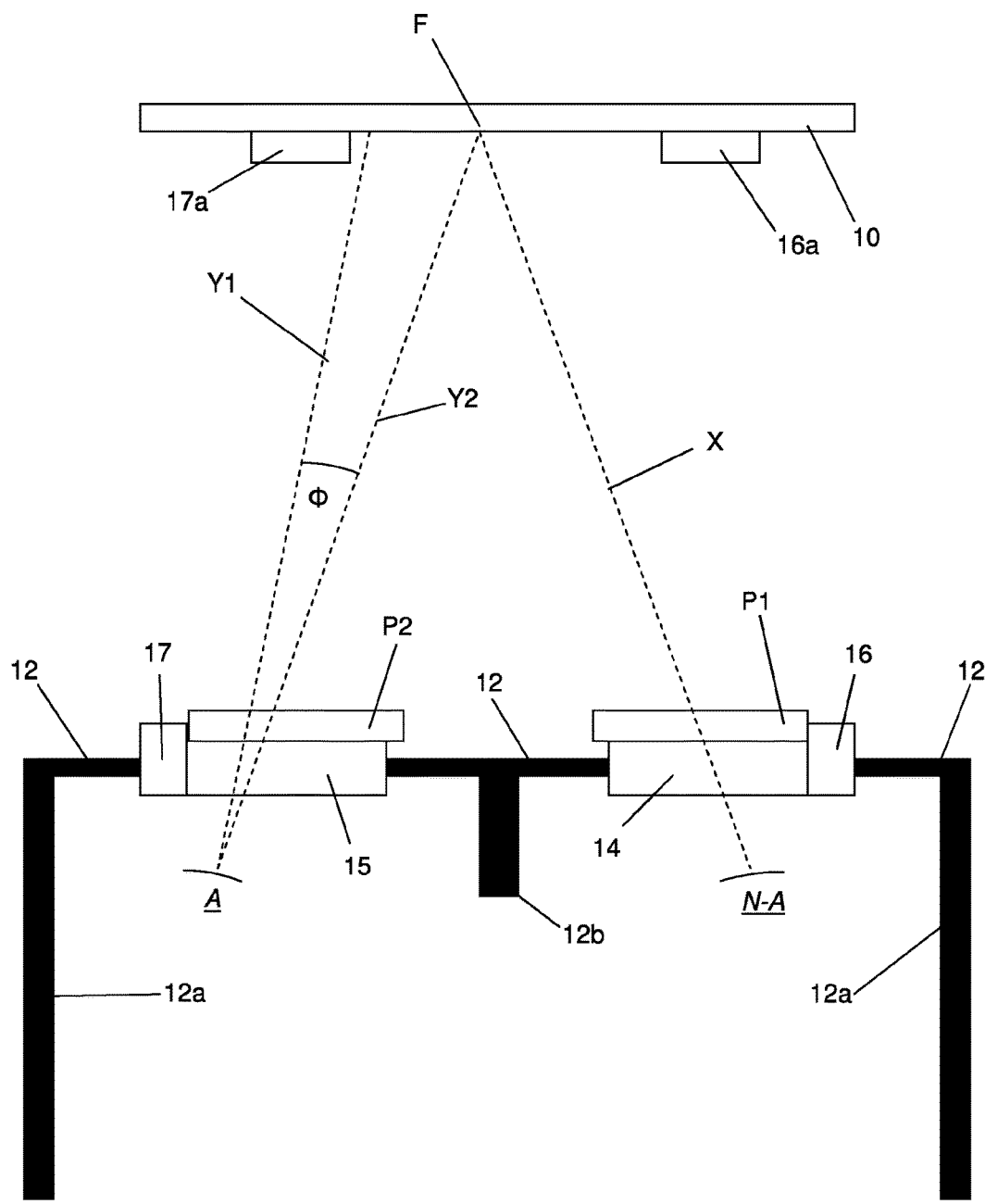
FIG. 1 is a schematic illustration of apparatus in accordance with the invention.

Referring first to FIG. 1, apparatus according to the invention is illustrated in a highly schematic manner, and comprises a visual display screen 10 that is viewed by a subject wearing a pair of shutter glasses, the frame of which is generally designated 12. The display screen 10 may have the form of a conventional computer screen or television display. The apparatus also comprises appropriate control and timing circuitry which may be generally conventional and is not described in detail here.

The shutter glasses comprise the frame 12 which is of generally conventional form and comprises side arms 12a that hold the shutter glasses in place on the subject's head. First and second eyeglasses 14,15 are held in the frame 12 and, in use, are positioned in front of the subject's eyes, which in the illustrated arrangement are a non-amblyopic eye N-A and an amblyopic eye A. A central barrier 12b extends from the frame 12 into close contact with the bridge of the subject's nose, and together with the side arms 12a ensures that each of the subject's eyes is able to see only through the eyeglass 14,15 positioned in front of it.

Eye-tracking video cameras 16,17 are mounted in the frame 12, adjacent to the eyeglasses 14,15, and are directed at the pupils of the respective eyes N-A,A so as to continuously monitor the direction of gaze of each eye. Alternatively, eye-tracking video cameras 16a,17a can be mounted in front of the screen 10 and track eye movements through the shutter glasses and the patient's own spectacle correction.

The eyeglasses 14,15 include a layer of liquid crystal material that becomes opaque in response to an applied electric potential, and is transparent in the absence of that potential. Each eyeglass 14,15 alternates at a frequency of 120 Hz, between opaque and transparent conditions, the first eyeglass 14 being opaque when the second eyeglass 15 is transparent, and vice versa.

In use, the subject is seated in front of the display screen 10 and views the images displayed upon that screen through the shutter glasses. First and second images are displayed alternately upon the screen 10, the alternation of those images being synchronised with the operation of the shutter glasses, such that the first image is viewed only by the subject's non-amblyopic eye N-A, and the second image is viewed only by the subject's amblyopic eye A. More specifically, the operation of the shutter glasses is matched to the refresh rate of the screen 10.

The first and second images that are alternately displayed on the screen 10, and that are viewed by the non-amblyopic and amblyopic eyes N-A,A are substantially identical, the images differing from each other only in the manner described below, ie the first image may contain some degradation of a fixation feature and the second image may be angularly displaced relative to the first image.

For larger angles of strabismus, prisms can be inserted into prism holder P1,P2 in front of the eyeglasses 14,15.

In a first mode of use of the apparatus, the first and second images are coincident and include a fixation feature. Where the images are static images, the fixation feature will usually, but not necessarily, be substantially central. Where, as in practice will be more common, the images are moving images, the fixation feature may move within the image, though it will occupy a substantially central region of the image for much of the time.

As illustrated in FIG. 1, the fixation feature (centred on the point F) is at the centre of the image and the non-amblyopic eye N-A fixes upon that feature, the direction of gaze being represented by the broken line X. The direction of gaze of the amblyopic eye A is represented by the broken line Y1, and that line is displaced from the fixation feature. The direction of gaze of each eye N-A,A is continuously monitored by the eye-tracking cameras 16,17 (or 16a,17a).

Figure 2:
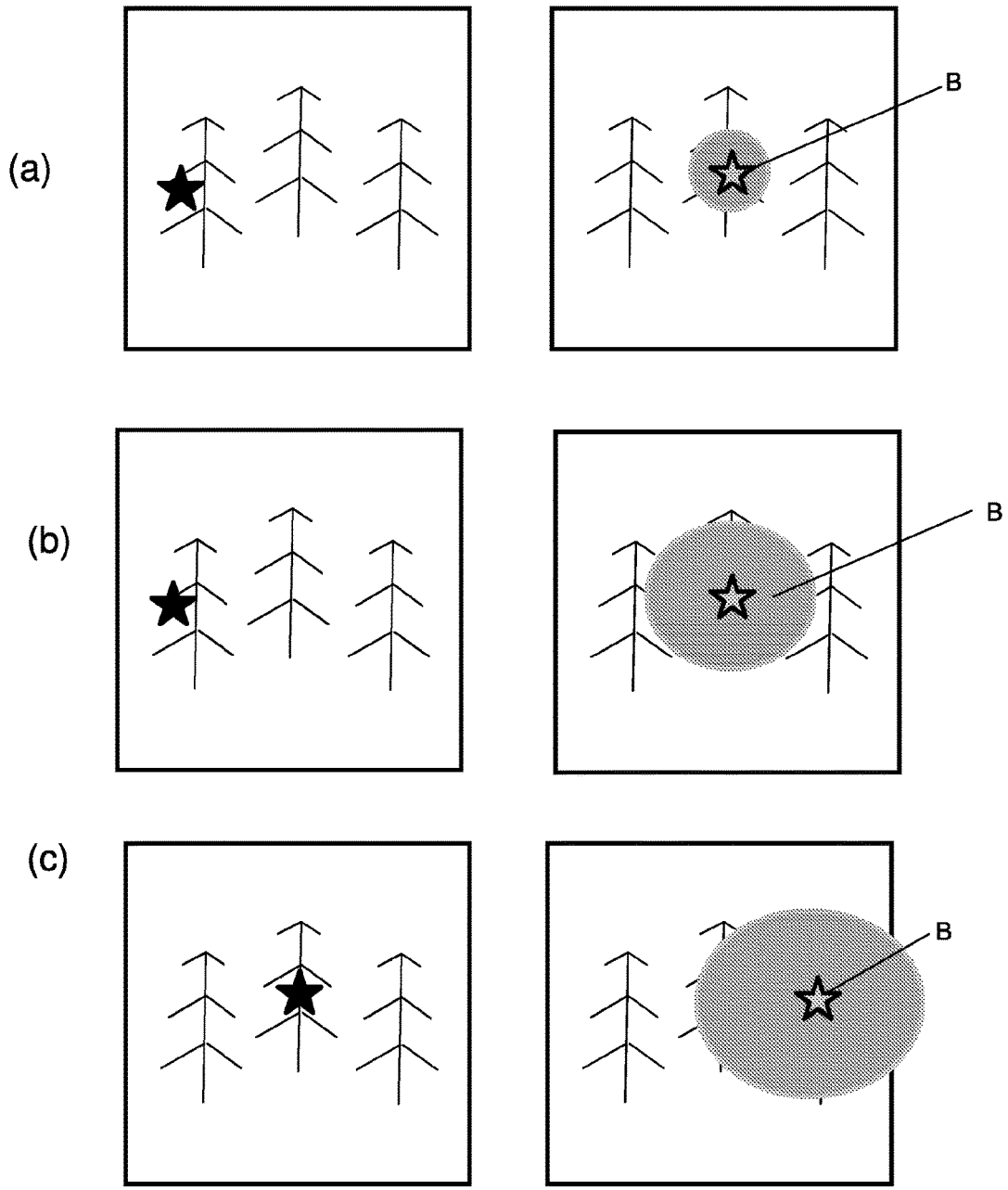
FIG. 2 illustrates schematically the steps involved in assessing the size of the central scotoma in the amblyopic eye of a subject with strabismic amblyopia.
Figure 2:
Figure 2:

The first mode of operation is illustrated in FIG. 2. In FIG. 2, the first and second images that are alternately displayed on the screen 10 are shown schematically side-by-side (but it will be understood that in practice the images are superimposed and coincident). The image on the right hand side, as viewed in each of FIGS. 2a, 2b and 2c is the first image, which is seen by the non-amblyopic eye N-A, and the image on the left hand side is the second image, which is seen by the amblyopic eye A.

The first and second images are initially (FIG. 2a) identical and contain a fixation feature in the central region of the image. The fixation feature is a region of high spatial frequency, and is illustrated schematically as a number of tree-like features. It should be noted that, although the first and second images in FIG. 2a are identical, the right-hand image (seen by the non-amblyopic eye N-A, which has greater visual acuity) will be perceived by the subject more clearly than the left-hand image (seen by the amblyopic eye A, which has impaired visual acuity).

In the first mode of operation, the apparatus is used to assess the size of the central scotoma of the amblyopic eye A. This is done by degrading the central part of the fixation feature in the first image, and progressively increasing the area of the degradation region. The degradation takes the form of blurring of the fixation feature. In the simplest approach, the degraded areas will, as illustrated in FIG. 2, have the luminance of all the pixels in the degraded region averaged, so that the degraded region appears as a region of uniform luminance (the grey area in FIG. 2), with minimal contrast. The area of degradation would be the equivalent of the image being passed through a low-bandwidth filter and the cut-off for the bandwidth can be set.

FIG. 2b illustrates the blurred area B with a diameter of intermediate size. FIG. 2c shows the blurred area B of large size. As described above, initially (FIG. 2a) it is the non-amblyopic eye N-A that fixes upon the fixation feature, the directions of gaze of the non-amblyopic and amblyopic eyes N-A, A being respectively along the lines X and Y1 in FIG. 1. As the size of the blurred region B increases, a point is reached at which fixation is taken up by the amblyopic eye A. That point is detected as a change in the direction of gaze of the amblyopic eye A, from line Y1 to line Y2 in FIG. 1. The size of the blurred area B at which that change is detected by the eye-tracking camera 17 is indicative of the size of the central scotoma of the amblyopic eye A.

In addition to providing a qualitative indication of the take-up of fixation by the amblyopic eye A, the change in the direction of gaze from Y1 to Y2 also provides an indication of the magnitude of the subject's strabismus, ie the angle of squint, represented in FIG. 1 by $\phi$.

An alternative approach is to keep the area of distortion fixed but to lower the upper point of cut-off for the low bandwidth filter, thereby sequentially removing more and more of the high spatial frequency end of the frequency range of the image. This would determine the degree, or depth, of the scotoma.

Figure 3:
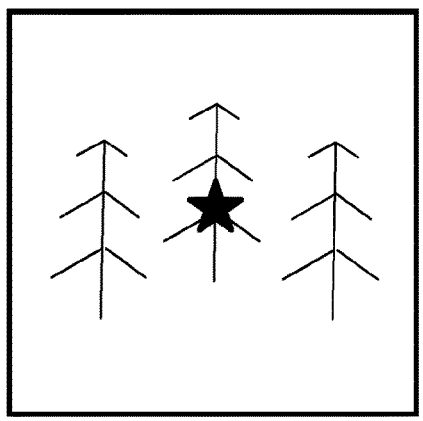
FIG. 3 illustrates the manner in which the apparatus in accordance with the invention may be used to treat strabismic amblyopia.
Figure 3:
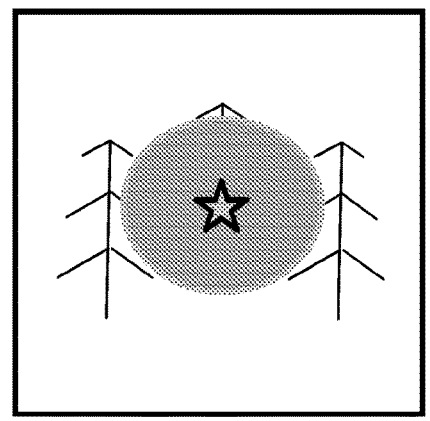
Figure 3:
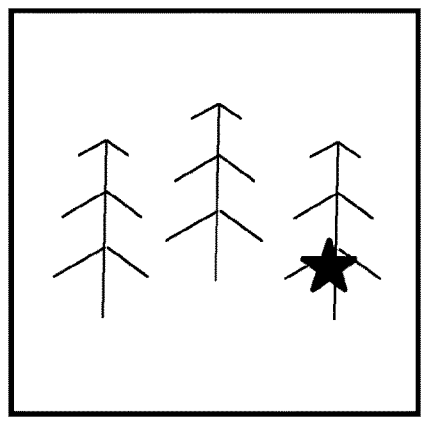
Figure 3:
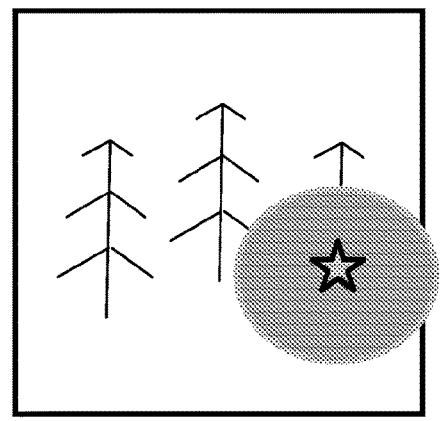
Figure 3:
Figure 3:

These pieces of information are utilised in a second mode of operation of the apparatus, which is schematically illustrated in FIG. 3. The images are now aligned so that the direction of gaze of both eyes land on the same point in the image. In this mode, the feature at the point of fixation is blurred (the size and degree of the amount of blurring having been determined by the first mode of operation) in the first image, which is viewed by the non-amblyopic eye N-A. The location of the point of fixation is determined by the eye-tracker and this determines the location of the area of degradation for the image viewed by the non-amblyopic eye N-A. In addition, the second image, viewed by the amblyopic eye A, is displaced relative to the first image by an angle that is equal to the measured angle of squint $\phi$. This ensures harmonious retinal correspondence, yet the blurring of the fixation feature in the first image ensures that the amblyopic eye A is stimulated.

Typically, the subject (who will most commonly be a child, often a small child of eight years of age or less) will view the images in the second mode of operation of the apparatus for protracted periods, perhaps of the order of hours at a time. To retain the subject's attention, the images may therefore be presented as an interactive computer game or an entertaining video or the like. Protracted use of the apparatus in this manner stimulates the central area of the amblyopic eye, thereby treating the amblyopia and leading to an improvement in ocular function.

The invention claimed is:

1. An apparatus for use in the treatment of strabismic amblyopia in a subject having a non-amblyopic eye that performs better and an amblyopic eye that performs worse, the amblyopic eye having a central scotoma, the apparatus comprising image presentation means adapted to display a first image to the non-amblyopic eye and a second image to the amblyopic eye, the first and second images being presented to the subject so as to be perceived as coincidental, wherein the first image and the second image include a common background, the apparatus further comprising eye-tracking means adapted to monitor the direction of gaze of the non-amblyopic eye and the amblyopic eye on the first and second images respectively, the apparatus further comprising means for creating a region of degradation located solely within a portion of the first image at the point of fixation of the first image, and for increasing the area of said region of degradation, wherein, in use of the apparatus, the non-amblyopic eye is fixed on the point of fixation prior to creation of the region of degradation and until the area of the region of degradation reaches a certain magnitude, whereupon the amblyopic eye takes up fixation, fixation of the amblyopic eye being indicated by a change in the direction of gaze of the amblyopic eye detected by the eye-tracking means, and the area of said region of degradation at which said take-up of fixation by the amblyopic eye occurs providing an indication of the size of the central scotoma of the amblyopic eye.

2. The apparatus as claimed in claim 1, wherein the first and second images are substantially identical, the images differing from each other only in that the first image may contain some degradation and the second image may be angularly displaced relative to the first image.

3. The apparatus as claimed in claim 1, wherein the first and second images are presented to the subject alternately, sufficiently rapidly as to be perceived to be simultaneously and continuously displayed.

4. The apparatus as claimed in claim 3, wherein the first and second images are presented separately to the user's eyes by an active shutter glass system, by a head-mounted display, or by other technology capable of dichoptic presentation.

5. The apparatus as claimed in claim 4, wherein an active shutter glass system is used that comprises a pair of eyeglasses arranged, in use, in front of the subject's eyes, each eyeglass incorporating a layer of liquid crystalline material that has the property of becoming opaque when a voltage is applied to it, being otherwise transparent (or vice versa).

6. The apparatus as claimed in claim 5, wherein the timing of the switching of each eyeglass between the opaque and transparent states is synchronized with the refresh rate of the visual display unit, and the first and second images are displayed alternately on the visual display unit.

7. The apparatus as claimed in claim 1, wherein fixation occurs on a part of the first and second images that has relatively high spatial frequency.

8. The apparatus as claimed in claim 7, wherein said part of the first and second images includes a regular pattern of visual elements such as lines or some other geometric pattern.

9. The apparatus as claimed in claim 7, wherein fixation occurs on a feature of the image that attracts the eye due to its significance in the context of the images.

10. The apparatus as claimed in claim 1, wherein the images are moving images.

11. The apparatus as claimed in claim 10, wherein the images form a video game and fixation occurs on a character in that game.

12. The apparatus as claimed in claim 1, wherein the degradation that is created in the first image is a blurring at the point of fixation.

13. The apparatus as claimed in claim 12, wherein another feature or features of the first image may also be selectively degraded.

14. The apparatus as claimed in claim 12, wherein the blurring occurs in a circular or generally circular area, the diameter of the blurred area gradually being increased until the amblyopic eye takes up fixation.

15. The apparatus as claimed in claim 12, wherein blurring is brought about using a low-pass filter constrained within a Gaussian envelope.

16. The apparatus as claimed in claim 12, wherein the blurring is brought about by averaging the luminance of the pixels within the region of distortion.

17. The apparatus as claimed in claim 12, which is capable of selectively blurring features of interest to the normal eye, such as a face or any other feature of interest.

18. The apparatus as claimed in claim 1, wherein the region of degradation is moved within the image according to the direction of gaze of the non-amblyopic eye.

19. A method for determining the size of the central scotoma of the amblyopic eye of a subject having a non-amblyopic eye that performs better and an amblyopic eye that performs worse, the method comprising presenting a first image to the non-amblyopic eye and a second image to the amblyopic eye, the first and second images being presented to the subject so as to be perceived as coincidental, and the first image and the second image including a common background, creating a region of degradation located solely within a portion of the first image within a fixation feature of the first image, and increasing the area of said region of degradation until the amblyopic eye takes up fixation, wherein the non-amblyopic eye is fixed on the fixation feature prior to creation of the region of degradation and until the area of the region of degradation reaches a certain magnitude, whereupon the amblyopic eye takes up fixation, the area of said region of degradation when the amblyopic eye takes up fixation providing an indication of the size of the central scotoma of the amblyopic eye.

20. The method as claimed in claim 19, wherein the taking up of fixation by the amblyopic eye is detected by tracking the movement of the amblyopic eye.

21. An apparatus for use in the treatment of strabismic amblyopia in a subject having a non-amblyopic eye that performs better and an amblyopic eye that performs worse, the amblyopic eye having a central scotoma, the apparatus comprising image presentation means adapted to display a first image to the non-amblyopic eye and a second image to the amblyopic eye, wherein the first image and the second image include a common background, the apparatus further comprising eye-tracking means adapted to monitor the direction of gaze of the non-amblyopic eye and the amblyopic eye on the first and second images respectively, the apparatus further comprising means for creating a region of degradation located solely within a portion of the first image within a fixation feature of the first image, and for increasing the area of said region of degradation, and the apparatus further comprising means for angularly displacing the second image relative to the first image by an angle corresponding to the subject's angle of squint, such that harmonious retinal correspondence is achieved, wherein, in a first mode of use of the apparatus, the non-amblyopic eye is fixed on the fixation feature prior to creation of the region of degradation and until the area of the region of degradation reaches a certain magnitude, whereupon the amblyopic eye takes up fixation upon the fixation feature, fixation of the amblyopic eye being indicated by a change in the direction of gaze of the amblyopic eye detected by the eye-tracking means, and the area of said region of degradation at which said take-up of fixation by the amblyopic eye occurs providing an indication of the size of the central scotoma of the amblyopic eye, and wherein, in a second mode of use of the apparatus, a region of degradation is created within the fixation feature of the first image, said region of degradation being of sufficient size to cause the amblyopic eye to take up fixation, and the second image is angularly displaced relative to the first image by an angle corresponding to the subject's angle of squint, such that harmonious retinal correspondence is achieved.

* * * * *